US00PP08511P

United States Patent [19]

Moore

[11] Patent Number: Plant 8,511

[45] Date of Patent: Dec. 21, 1993

[54] GRAPEVINE—SUNBELT CULTIVAR

[75] Inventor: James N. Moore, Fayetteville, Ark.

[73] Assignee: University of Arkansas, Fayetteville, Ark.

[21] Appl. No.: 951,132

[22] Filed: Sep. 25, 1992

[51] Int. Cl.[5] ..... A01H 5/00

[52] U.S. Cl. ..... Plt./47.1

[58] Field of Search ..... Plt./47.1

[56] References Cited

PUBLICATIONS

Voss, Donald H., 1992 "Relating Colorimeter Measurement of Plant Color to the *Royal Horticultural Society Colour Chart*" *HortScience* vol. 27 (12) pp. 1256–1260.

*Primary Examiner*—James R. Feyrer

[57] ABSTRACT

Description and specifications of a new and distinct grapevine variety which originated from the germination of open-pollinated seeds of the Concord cultivar (non-patented) are provided. This new grapevine variety can be distinguished by its production of evenly colored fruits in high temperature climates, its outstanding quality in juice and jellies, and its good resistance to foliar and fruit diseases.

2 Drawing Sheets

SUMMARY OF THE INVENTION

The new and distinct variety of grapevine originated from open-pollinated seeds of Concord (non-patented), collected in 1968 at the Arkansas Agricultural Expermiment Station experimental vineyard at Clarksville, Ark. The seeds resulting from this collection were germinated in a greenhouse during the winter of 1968–69. Resulting seedlings were planted in the spring of 1969 in a field on the Arkansas Agricultural Experiment Station at Clarksville, Ark. The seedlings fruited in the summer of 1971 and one, designated Ark. 1335, was selected for its resistance to diseases, its ability to ripen its fruits evenly under high temperatures, and its high quality juice products.

During 1972, the original plant selection was propagated asexually by rooting hardwood cuttings and a test planting of four vines was established at the above noted location. Subsequently, larger test plantings have been established with asexually multiplied vines at four additional locations in Arkansas and on state agricultural experiment stations in Kentucky, Louisiana, Minnesota, North Carolina, New York, Missouri, Texas, Puerto Rico, and Brazil.

The new variety has been asexually propagated annually since 1972 by the rooting of both hardwood and softwood cuttings and by grafting onto rootstocks. Its roots readily from both hardwood and softwood cuttings and no graft incompatibility has been observed. During all types of asexual multiplication, the vegetative and fruit characteristics of the original plant have been maintained.

Test plantings over a wide geographic area have shown this new variety to be widely adapted to differing soil and climatic conditions. It has shown above average winter hardiness in Northern areas. The canes mature their wood early and enter winter in a well-hardened condition. In Southern areas where high temperatures prevail during fruit maturation, the berries ripen evenly within the clusters, in contrast to the Concord variety which shows extensive uneven ripening under such conditions.

Vines of the new variety are vigorous and typically characteristic of *Vitis labrusca.* It has produced well as own-rooted plants in all locations tested.

A distinctive feature of the new variety is its resistance to common fungus diseases of grapevines. Under minimum chemical disease control, the vines and fruit have demonstrated outstanding resistance to black rot (*Guignardia bidwellii* (Ell.) V. & R.), anthracnose (*Elsinoe ampelina* (d. By.) Sher), powdery mildew (*Uncinula necator* Burr.) and downy mildew (*Plasmopora viticola* Berl. & Tomi.). The fruit has shown no inclination to split following rains. Another distinctive feature of the new variety is its ability to ripen fruit evenly under high temperature conditions.

The new variety ripens its fruit late, about the same time as the Concord cultivar. The average ripening data is August 13 in central Arkansas. The fruit quality is maintained well on the vine after maturity. Berries adhere well to the fruit pedicels and do not shatter from the clusters.

The fruit is blue in color at maturity and evenly colored within the cluster. The fruit shape is round. Fruit skins are thick and do not adhere to the flesh. The berries are large in size ca. 4.5 g). The flavor is strong and typically labrusca in character, resembling closely that of the variety Concord. Soluble solids concentration of the juice at fruit maturity average 16.4%, with pH of 2.97 and acidity of 0.86. At equal soluble solids, juice of the new variety is low in pH and higher in acidity than the Concord variety. Juice color of the new variety is darker, more red, and contains more monomeric anthocyanin pigments than the Concord variety. Sensory ratings of juice of the new variety are higher in color and aroma than the Concord variety, with no difference in the two juices in flavor or overall acceptability.

Fruit clusters, borne usually two per shoot, are small in size (ca. 145 g), well-filled, and compact and resemble the clusters of the Concord variety. Fruit cluster peduncles are short and the clusters form close to the supporting shoots.

The new variety has been named the SUNBELT cultivar.

BRIEF DESCRIPTION OF THE PHOTOGRAPHS

The accompanying photographs show typical specimens of the fruit and leaf of the new variety in color as nearly true as it is reasonable possible to make in a color illustration of this character.

DETAILED DESCRIPTION OF THE NEW VARIETY

The following is a detailed description of the botanical and pomological characteristics of the subject grapevine. Color data are readings from a Minolta Chroma Meter CR-200, version 3.0 which measures absolute chromaticity in tristimulus values X,Y, and Z as determined by the Commission Internationale de l-Eclairage. Color was determined using the CIE L*a*b* system. Calibration was performed using a standard white plate supplied by the manufacturer. These color data are supplemented with Royal Horticultural Society Colour Chart designations obtained by computer matching of electronic readings to R.H.S. color references.

Where dimensions, sizes, colors and other characteristics are given, it is to be understood that such characteristics are approximations of averages set forth as accurately as practicable.

The descriptions reported herein are from specimens grown at Clarksville, Ark. unless otherwise noted.

Vine:

*Size.*—Large.

*Growth.*—Vigorous, bud break March 30, growth cessation in early fall.

*Productivity.*—Medium (10-MT/ha on mature vines).

*Cold hardiness.*—Good, equal to Concord variety.

*Canes.*—Large diameter, long, not upright in growth habit. Diameter of mature cane: base 1.02 cm, midpoint 0.77 cm, terminal 0.39 cm. Internode length: base 12.50 cm, midpoint 15.54 cm. terminal 9.96 cm. Color of mature cane: base L=34.32, a=+14.35, b=+13.84 Greyed-Orange (166A); midpoint L=36.64, a=+13.32, b=+14.02 Greyed-Orange (166A) terminal L=36.01 a=+11.95, b=+13.15 Greyed-Orange (166A). Diameter of young shoots in spring (6–12"): base 7.45 mm, midpoint 4.91 mm, terminal 2.29 mm. Internode length 43.8 mm.

*Disease resistance.*—Good resistance to fungus diseases black rot, downy mildew, powdery mildew, and anthracnose.

Foliage:

*Leaves.*—Color of mature leaves: base abaxial: L=51.37, a=−6.63, b=23.40 Yellow-Green (148A), adaxial L=35.01, a=−11.58, b=16.96 Yellow-Green (147A); midpoint abaxial L=49.33, a=−11.33, b=23.89 Yellow-Green (147B), adaxial L=33.72. a=−11.62, b=15.52 Yellow-Green (147A); terminal abaxial L=54.38, a=−10.22, b=30.02 Yellow-Green (146B), adaxial L=46.12, a=−15.81, b=30.76 Yellow-Green (146B). Color of petioles L=33.39, a=10.38, b=12.98 Brown (200C). Sinus of mature leaf is 10.85 cm deep and 12.38 cm at widest point. Mature leaves have a light amount of pubescence on adaxial surface. Color of young (unfolded) leaves: base abaxial L=50.64, a=−13.43, b=24.82 Yellow-Green (146B); adaxial L=41.37, a=−17.26, b=27.86 Yellow-Green (146A); midpoint abaxial L=52.72, a=−9.43, b=20.15 Yellow-Green (148B); adaxial L=43.98, a=−15.47, b=28.74 Yellow-Green (146A): terminal abaxial L=60.58, a=−1.51, b=13.07 Greyed-Green (197C); adaxial L=54.79, a=−12.78, b=34.80 Yellow-Green (146C). Color of petioles of young leaves L=43.33, a=−1.85, b=17.82 Greyed-Green (197A).

Flowers:

*Date of bloom.*—May 12.

*Shape of cluster.*—Cylindrical, conical shape with small shoulder.

*Size of cluster.*—Length: 14.3 cm. Width: 8.1 cm.

*Reproductive organs.*—Stamens — numerous and erect. Pistils — medium long. Pollen — normal, abundant, and fertile.

Fruit:

*Maturity.*—Late, similar to Concord. Average ripe date is August 13, Even ripening in cluster.

*Size.*—Large, avg. 4.5 g, uniform in size.

*Shape.*—Spherical, uniform shape.

*Color.*—Very similar to Concord. At maturity: with bloom, Blue Group (102C); without bloom, Blue Group (103A).

*Skin.*—thick, non-adhering to flesh.

*Seeds.*—Number: 2–4 per berry, avg. 2.64. Size: Large, similar to Concord. Length: 1 cm; width: 5 mm; with pronounced beak. Color: Brown Group (200C).

*Brush length.*—6.01 mm.

*Peduncle length.*—29.90 mm.

*Flavor.*—Typically labrusca, strong, similar to Concord.

*Juice.*—Darker and more red in color than Concord (optical density 0.469 vs. 0.174). Lower pH (2.97 vs. 3.42 and higher acidity (0.86% vs. 0.67%) than Concord.

*Soluble solids.*—16.4%, similar to Concord.

*pH.*—2.97, lower than Concord.

*Total acids.*—0.86%, higher than Concord.

*Mature cluster weight.*—145 g.

*Berries per cluster.*—35.

*Cluster per vine.*—83.

*Clusters per shoot.*—Usually 2.

*Uses.*—Production of high quality juice and jelly. Can also be fermented into wine or consumed fresh. Especially adapted to areas with high temperatures during fruit ripening in which no adapted juice grape varieties now exist.

The Variety

The most distinctive features of the variety are its ability to ripen fruit uniformly under high temperatures, its outstanding quality in processed products, and its resistance to fungus diseases.

I claim:

1. A new and distinct variety of grapevine, substantially as illustrated and described, characterized by its even coloration of fruit during ripening under high temperatures, outstanding juice and jelly qualities, and high resistance to common grape fungal pathogens.

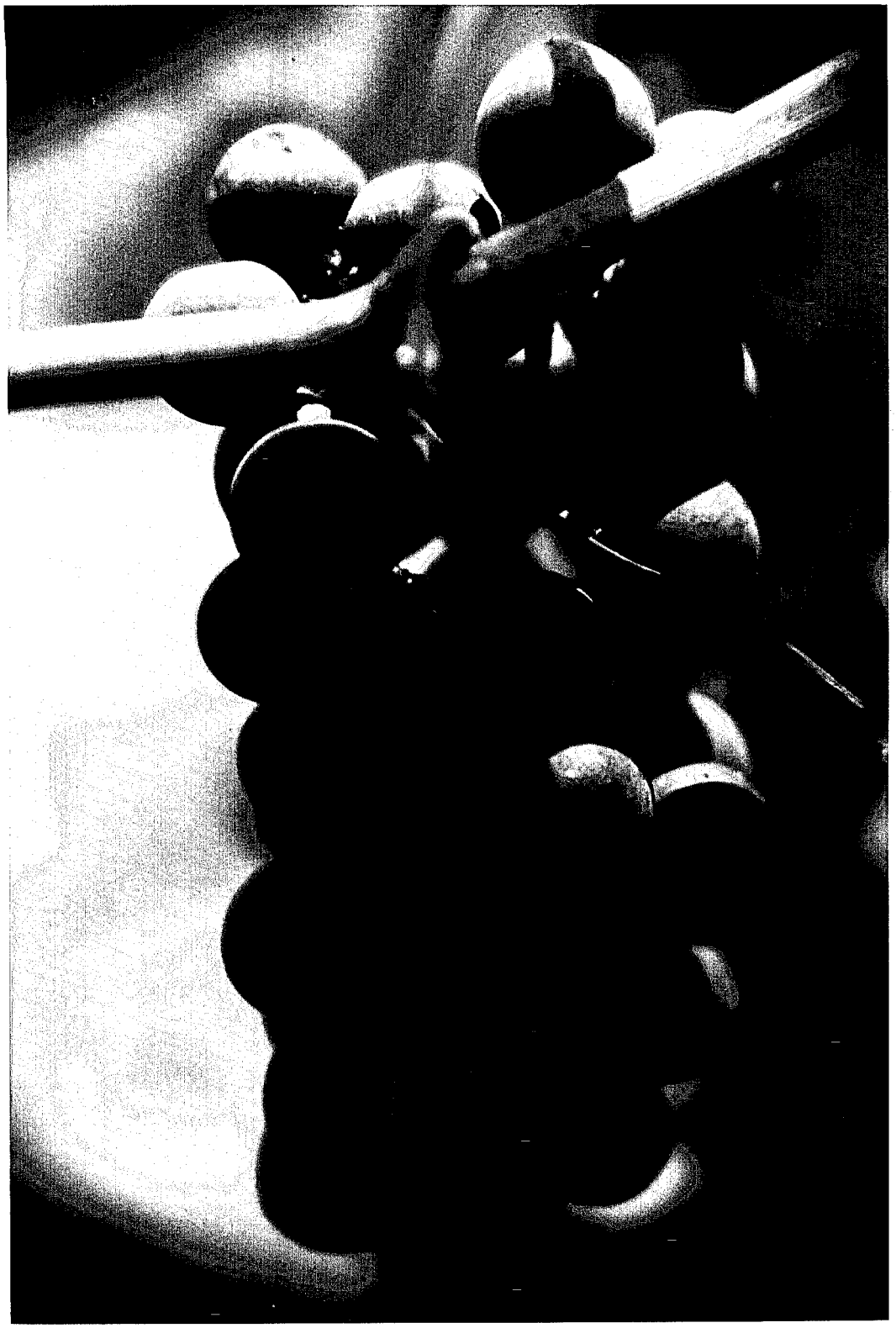

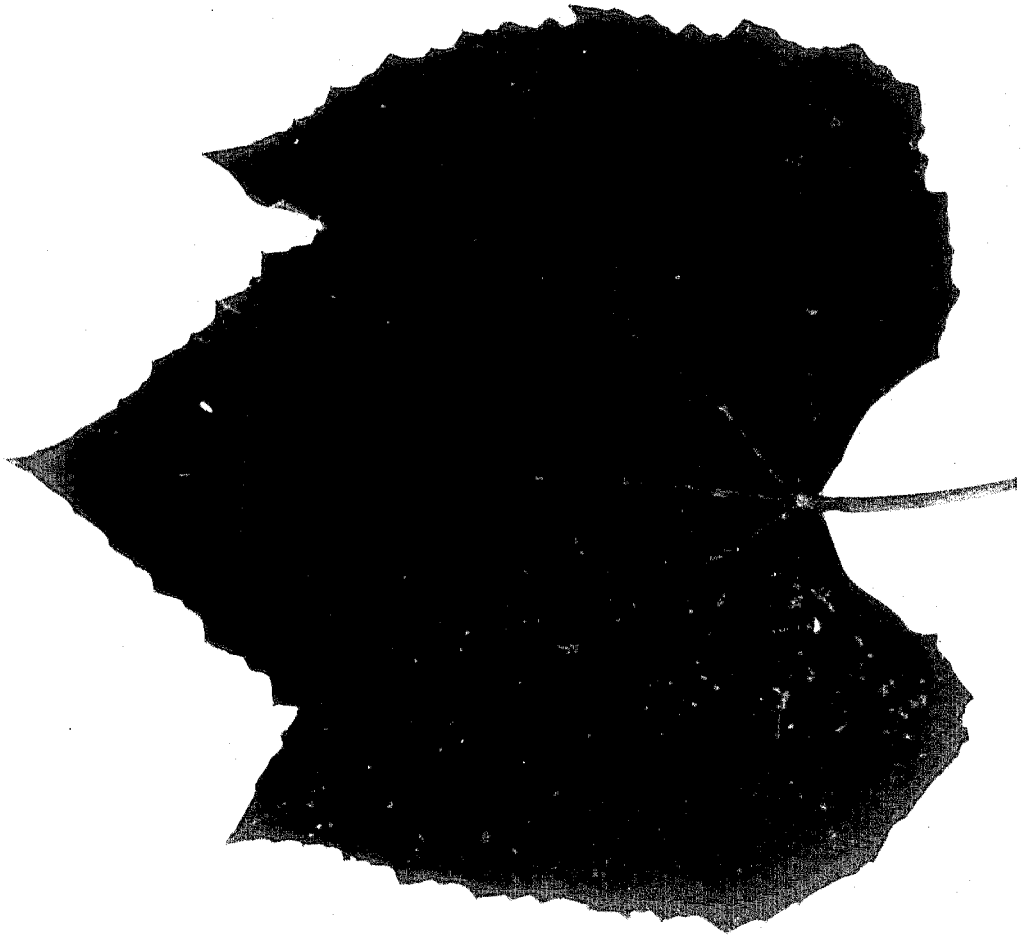

* * * * *